(12) United States Patent
Cavuto et al.

(10) Patent No.: US 11,141,608 B2
(45) Date of Patent: Oct. 12, 2021

(54) COMPACT PROTON BEAM ENERGY MODULATOR

(71) Applicant: Massachusetts Institute of Technology, Cambridge, MA (US)

(72) Inventors: Matthew L. Cavuto, Skillman, NJ (US); Neerja Aggarwal, Cambridge, MA (US); Melissa Li, Johns Creek, GA (US); Nathaniel H. Rodman, Corvallis, OR (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 16/483,605

(22) PCT Filed: Apr. 6, 2018

(86) PCT No.: PCT/US2018/026443
§ 371 (c)(1),
(2) Date: Aug. 5, 2019

(87) PCT Pub. No.: WO2018/187680
PCT Pub. Date: Oct. 11, 2018

(65) Prior Publication Data
US 2020/0094076 A1 Mar. 26, 2020

Related U.S. Application Data

(60) Provisional application No. 62/482,743, filed on Apr. 7, 2017.

(51) Int. Cl.
*A61N 5/10* (2006.01)
*A61B 6/00* (2006.01)
(Continued)

(52) U.S. Cl.
CPC .......... *A61N 5/1067* (2013.01); *A61B 6/5205* (2013.01); *G06T 11/008* (2013.01); *G21K 5/04* (2013.01); *A61N 2005/1087* (2013.01)

(58) Field of Classification Search
USPC .......................................... 250/505.1, 492.3
See application file for complete search history.

(56) References Cited

U.S. PATENT DOCUMENTS

| | | | |
|---|---|---|---|
| 5,668,371 A | 9/1997 | Deasy et al. | |
| 5,825,845 A | 10/1998 | Blair et al. | |

(Continued)

FOREIGN PATENT DOCUMENTS

WO    WO 2016/016653 A1    2/2016

OTHER PUBLICATIONS

International Preliminary Report on Patentability dated Oct. 17, 2019 for International Application No. PCT/US2018/026443; 9 Pages.

(Continued)

*Primary Examiner* — Kiet T Nguyen
(74) *Attorney, Agent, or Firm* — Daly, Crowley, Mofford & Durkee, LLP

(57) ABSTRACT

A proton beam imaging system includes: a proton beam generator to generate a proton beam; a proton beam modulator through which the proton beam passes positioned between the proton beam generator and an image target; and a proton beam detector positioned to detect the proton beam existing the image target; wherein the proton beam modulator comprises: a rotating wheel having an axis of rotation positioned so that the proton beam passes through the axis of rotation and the axis of rotation is perpendicular to the proton beam; a first modulating portion comprising a first material portion and a second material portion through which a proton beam passes; and a second modulating (Continued)

portion comprising a third material portion and a fourth material portion through with the proton beam passes; wherein the first and second wedges are positioned opposite each other on the rotating wheel.

22 Claims, 14 Drawing Sheets

(51) Int. Cl.
*G06T 11/00* (2006.01)
*G21K 5/04* (2006.01)

(56) References Cited

U.S. PATENT DOCUMENTS

| | | | |
|---|---|---|---|
| 6,034,377 | A | 3/2000 | Pu |
| 7,977,648 | B2 | 7/2011 | Westerly et al. |
| 7,977,656 | B2 | 7/2011 | Fujimaki et al. |
| 8,129,701 | B2 | 3/2012 | Al-Sadah et al. |
| 8,330,132 | B2 | 12/2012 | Guertin et al. |
| 2008/0067405 | A1 | 3/2008 | Nihongi et al. |
| 2008/0135361 | A1 | 6/2008 | Zhou et al. |
| 2009/0299634 | A1* | 12/2009 | Schaffner ............ A61N 5/1048 702/1 |
| 2010/0019167 | A1 | 1/2010 | Al-Sadah et al. |
| 2011/0280357 | A1 | 11/2011 | Stevenson |
| 2012/0228493 | A1 | 9/2012 | Gottschalk et al. |
| 2014/0094643 | A1* | 4/2014 | Gall .................. A61N 1/44 600/2 |
| 2015/0041665 | A1 | 2/2015 | Hollebeek et al. |
| 2015/0099918 | A1 | 4/2015 | Takayanagi et al. |
| 2015/0293235 | A1 | 10/2015 | Cameron et al. |

OTHER PUBLICATIONS

PCT International Search Report and Written Opinion dated Jul. 2, 2018 for International Application No. PCT/US2018/026443; 10 Pages.

International Atomic Energy Agency (IAEA); "Absorbed Dose Determination in External Beam Radiotherapy;" An International Code of Practice for Dosimetry Based on Standards of Absorbed Dose to Water; Technical Reports Series No. 398; Jan. 2000; 242 Pages.

Jee et al., "Investigation of Time-Resolved Proton Radiography Using X-Ray Flat-Panel Imaging System;" Physics in Medicine and Biology, vol. 62, No. 5; Feb. 9, 2017; 16 Pages.

Newhauser et al., "The Physics of Proton Therapy;" Physics in Medicine and Biology, vol. 60, No. 8; Mar. 24, 2015; pp. R155-R209; 55 Pages.

Siegel et al., "Cancer Statistics, 2016;" CA: A Cancer Journal for Clinicians, vol. 66, No. 1; Jan. 2016; pp. 7-30; 24 Pages.

Valdivieso et al., "Cancer Survivors in the United States: A Review of the Literature and a Call to Action;" International Journal of Medical Sciences, vol. 9, No. 2; Jan. 17, 2012; pp. 163-173; 11 Pages.

Zhang et al., "Calculation of Water Equivalent Thickness of Materials of Arbitrary Density, Elemental Composition and Thickness in Proton Beam Irradiation;" Physics in Medicine and Biology, vol. 54, No. 6; Mar. 2009; pp. 1383-1395; 13 Pages.

* cited by examiner

COMPACT PROTON BEAM ENERGY MODULATOR

RELATED APPLICATIONS

This patent application is a U.S. National Stage of PCT application number PCT/US2018/026443 filed in the English language on Apr. 6, 2018, and entitled "COMPACT PROTON BEAM ENERGY MODULATOR," which claims priority to and benefit of U.S. Provisional Patent Application No. 62/482,743 (filed Apr. 7, 2017), which is incorporated here by reference in its entirety.

BACKGROUND

Proton beams are used in medical applications to apply radiation treatment to areas of a patient's body. For example, a proton beam may be applied to a cancerous tumor with more precision than standard radiation techniques. Using a proton beam for treatment may reduce or eliminate radiation damage to tissues surrounding the targeted tumors. This is due, at least in part, to a proton's ability to deliver a radiation dose to a very small and condensed area compared to other radiation delivery techniques.

Treatment consists of directing high energy protons into a patient's body such that the protons deposit their radiation energy inside the tumor. Prior to treatment, the tumor and surrounding area must be imaged. Typically, photon-based imaging techniques like x-ray have been used. However, the photons used by these techniques differ from the protons used for delivery of treatment and interact with the tissue differently. Thus, using a photon-based imaging system to guide the proton-based treatment may introduce a margin of error.

SUMMARY

For certain applications, it may be beneficial to provide a proton beam modulator to meet one or more of the following goals: a minimum modulation range of 25 cm WET, a maximum period of full range modulation less than 300 ms, a constant scattering angle during modulation, a minimum energy step resolution of 2 mm WET, a maximum random error of less than 0.5 mm WET, the ability to stop the beam entirely once per cycle period, a modulator size that may fit within a 10 cm cube, the ability to accommodate a 0.5 cm beam diameter, balanced weight around an axis of rotation to minimize vibration during rotation, ability to operate in a vacuum, and the ability to let a proton beam pass through the modulator unobstructed.

In embodiments, a proton beam modulator includes a first modulating portion comprising a first material portion and a second material portion through which a proton beam passes; and a second modulating portion comprising a third material portion and a fourth material portion through which the proton beam passes; wherein the first and second modulating portions are positioned opposite each other on a rotating wheel.

One or more of the following features may be included:

The rotating wheel may be positioned so that the proton beam passes through a center of rotation of the rotating wheel.

The rotating wheel may be positioned so that an axis of rotation of the rotating wheel is perpendicular to the proton beam.

The first modulating portion and the second modulating portion may be positioned to create an open channel through the modulator so that, when the channel is parallel to the proton beam, the proton beam can pass through the open channel without passing through the first and second modulating portion.

The first modulating portion may have a wedge shape.

The first material portion and the second material portion are arranged radially from a center of rotation of the wheel so that the second material portion is inside the first material portion.

A thickness of the wedge shape may decrease along an angular coordinate of the wedge shape.

A thickness of the first material portion may decreases along the angular coordinate of the wedge shape and a thickness of the second material portion may increase along the angular coordinate of the wedge shape.

The combination of the first, second, third, and fourth material portions may modulate an energy level of the proton beam and a scattering of the proton beam.

The combination of the first, second, third, and fourth material portions may modulate the energy level of the proton beam such that the energy level of the proton beam changes as the modulator rotates.

The first and second modulating portions are each provided having a wedge shape.

The first and second modulating portions are each provided having a wedge shape and produce an energy modulation in the range of about 12 cm WET to about 32 cm WET.

The combination of the first, second, third, and fourth material portions may modulate the scattering of the proton beam so that the scattering remains substantially constant as the modulator rotates.

A circular plate may be positioned so that the first modulating portion and the second modulating portion are sandwiched between the rotating wheel and the circular plate.

The first and second modulating portions may be removable from the rotating wheel and the circular plate.

The first and third material portions may comprise stainless-steel.

The second and fourth material portions may comprise lead.

The rotating wheel may have a diameter of 10 cm or less.

In another embodiment, a proton beam imaging system includes: a proton beam generator to generate a proton beam; a proton beam modulator through which the proton beam passes positioned between the proton beam generator and an image target; and a proton beam detector positioned to detect the proton beam existing the image target; wherein the proton beam modulator comprises: a rotating wheel having an axis of rotation positioned so that the proton beam passes through the axis of rotation and the axis of rotation is perpendicular to the proton beam; a first modulating portion comprising a first material portion and a second material portion through which a proton beam passes; and a second modulating portion comprising a third material portion and a fourth material portion through with the proton beam passes; wherein the first and second wedges are positioned opposite each other on the rotating wheel.

One or more of the following feature may be included:

The first and third material portions may comprise stainless-steel, and the second and fourth material portions may comprise lead.

The first and third material portions may comprise a wedge shape having a varying thickness to modulate an energy level of the proton beam as the proton beam modulator rotates, wherein the proton beam may be modulated to have a varying energy level as the proton beam modulator rotates.

The second and fourth material portions may comprise a wedge shape having a varying thickness to modulate a degree of scattering of the proton beam as the proton beam modulator rotates, wherein the proton beam may be modulated to have a substantially constant degree of scattering as the proton beam modulator rotates.

The proton beam imaging system may comprise a gantry portion, wherein the proton beam modulator is situated within the gantry portion.

In embodiments, a proton beam modulator includes a plurality of wedge-shaped modulating portions, each of the plurality of wedge-shaped modulating portions comprising a first material portion and a second material portion configured such that in response to a proton beam incident thereon, at least portions of the proton beam are capable of passing therethrough and wherein the of the plurality of wedge-shaped modulating portions are disposed in spatial relation such that the plurality of wedge-shaped modulating portions define an axis of rotation positioned such that an axis along which a proton beam is aligned is perpendicular to the axis of rotation defined by the plurality of wedge-shaped modulating portions.

In embodiments, the plurality of wedge-shaped modulating portions are provided as a pair of modulating portions positioned opposite each and define an axis of rotation positioned such that an axis along which a proton beam is aligned is perpendicular to the axis of rotation defined by the pair of wedge-shaped modulating portions.

BRIEF DESCRIPTION OF THE DRAWINGS

The foregoing features may be more fully understood from the following description of the drawings. The drawings aid in explaining and understanding the disclosed technology. Since it is often impractical or impossible to illustrate and describe every possible embodiment, the provided figures depict one or more exemplary embodiments. Accordingly, the figures are not intended to limit the scope of the invention. Like numbers in the figures denote like elements.

DETAILED DESCRIPTION

Figure 1:
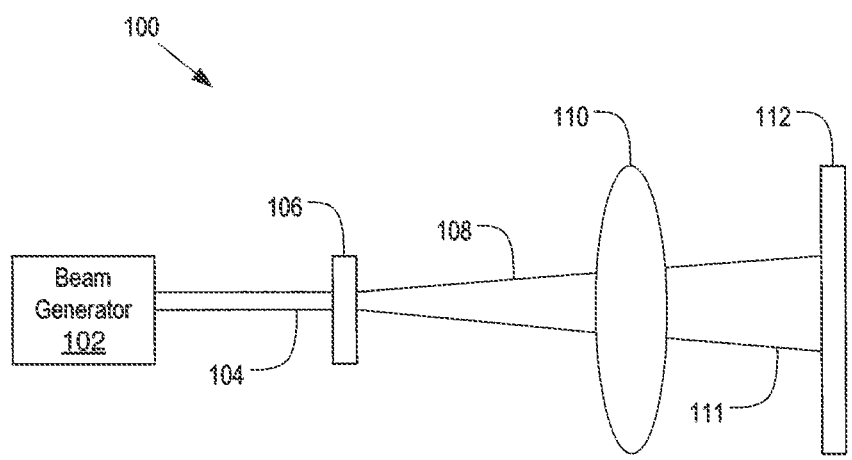
FIG. 1 is a block diagram of a proton beam imaging system.

FIG. 1 is a block diagram of a proton beam imaging system 100. Proton beam imaging system 100 includes a beam generator 102 which generates a proton beam 104. Proton beam 104 may be a columnar beam with a fixed or variable energy level.

Modulator 106 may comprise a quantity of material through which proton beam 104 passes. As it passes through, proton beam 104 may lose energy due to dissipation or blocking by modulator 106. Modulator 106 may also scatter the protons in beam 104. As a result, the incident beam 108 that passes through modulator 106 may have a lower energy level (due to dissipation) and a wider area (due to scattering) than proton beam 104.

Incident beam 108 may then pass through target 110, which may also affect the energy level and scattering profile of beam 108. In embodiments, target 110 may be the item to be imaged by proton imaging system 100. If proton imaging system 100 is used in a medical imaging application, for example, target 110 may be a portion of a patient's body.

A proton detector array 112 may detect proton beam 111 exiting target 110. Once detected, the signals produced by proton detector array 112 may be processed (e.g. by a general purpose or image processor) to produce an image of target 110.

Proton beam generator 102 may be housed in a gantry (not shown). For example, if the proton beam imaging system is a medical imaging system, a gantry may be suspended in or around a patient bed or examination table. In embodiments, the proton beam modulator may also be situated in the gantry so that proton beam 104 exits the gantry having already been modulated.

Figure 2:
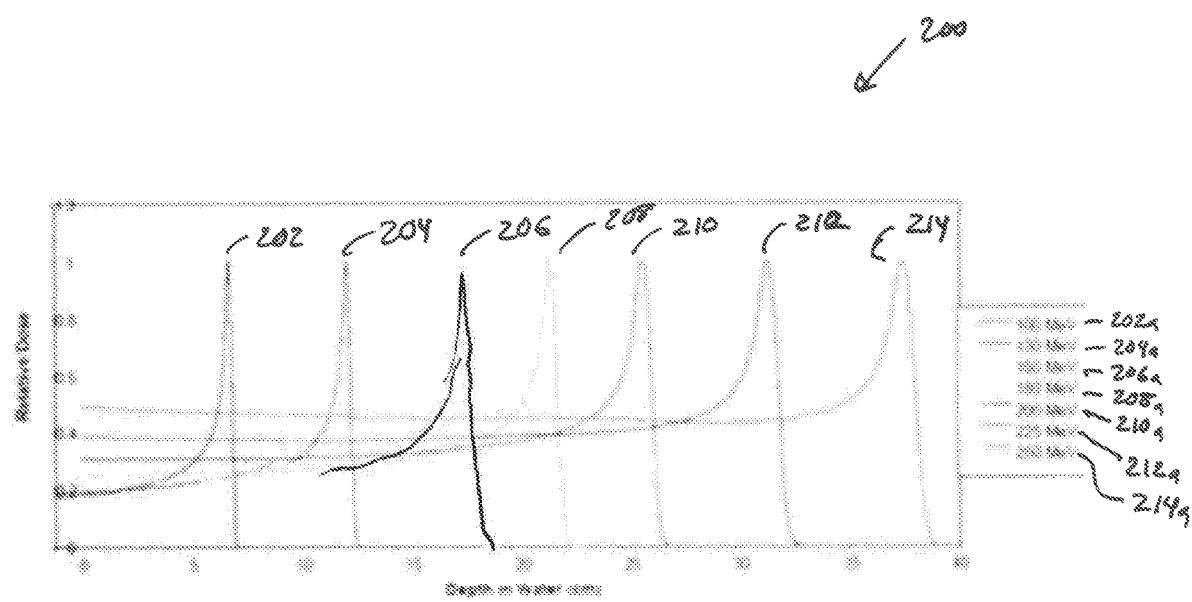
FIG. 2 is a graph of radiation from proton beams.

Referring to FIG. 2, materials through which a proton passes may be qualified with a water equivalent thickness ("WET") that indicates how much energy the material will dissipate from the proton as the proton passes through the material. Graph 200 illustrates the WET concept. The horizontal axis represents depth (in cm) through which a proton travels through water. The vertical axis represents radiation given off by the proton.

When the energy of a proton is almost depleted, the proton delivers a maximum dosage of radiation called a Bragg peak. Peaks (e.g. peaks 202-214) represent the Bragg peaks of protons having various levels of initial energy. A proton with greater initial energy will travel further through water than a proton with relatively less initial energy. For example, peak 202, which occurs at about 6 cm of water depth, results from a proton having 100 MeV of energy (as shown by reference number 202a). Peak 214, which occurs at about 37 cm of water depth, results from a proton having 250 MeV of energy (as shown by reference number 214a). The other peaks result from protons having energy levels between 100 MeV and 250 MeV, as indicated by their respective energy levels labeled 202a-214a.

Figure 3:
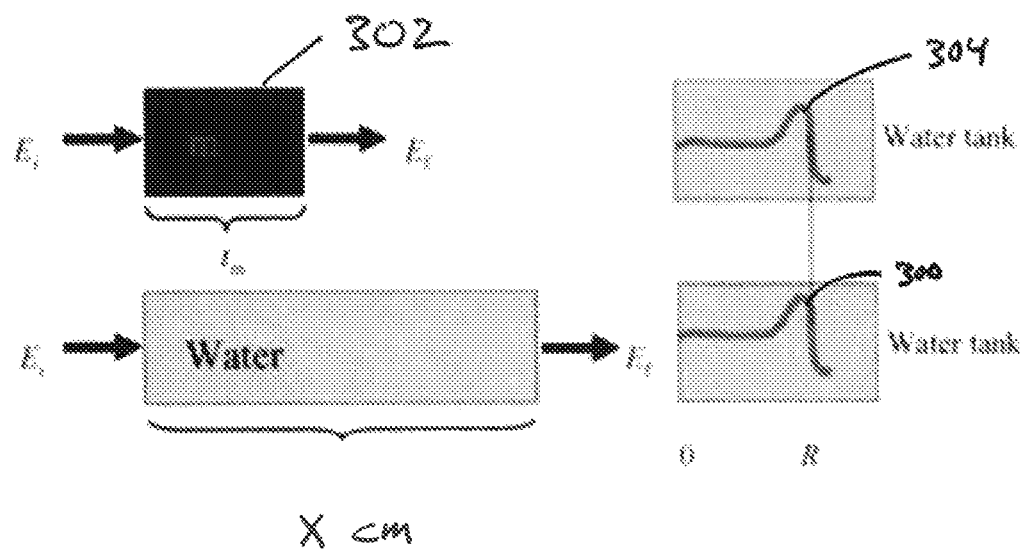
FIG. 3 is a block diagram illustrating water-equivalent thickness (WET).

Referring to FIG. 3, materials may be qualified by their WET rating. In FIG. 3, a proton passing through X cm of water results in Bragg peak 300. Similarly, a proton passing through material 302 results in Bragg peak 304. Because Bragg peaks 300 and 304 are the same, material 302 may be said to have a WET value of X cm.

Figure 4:
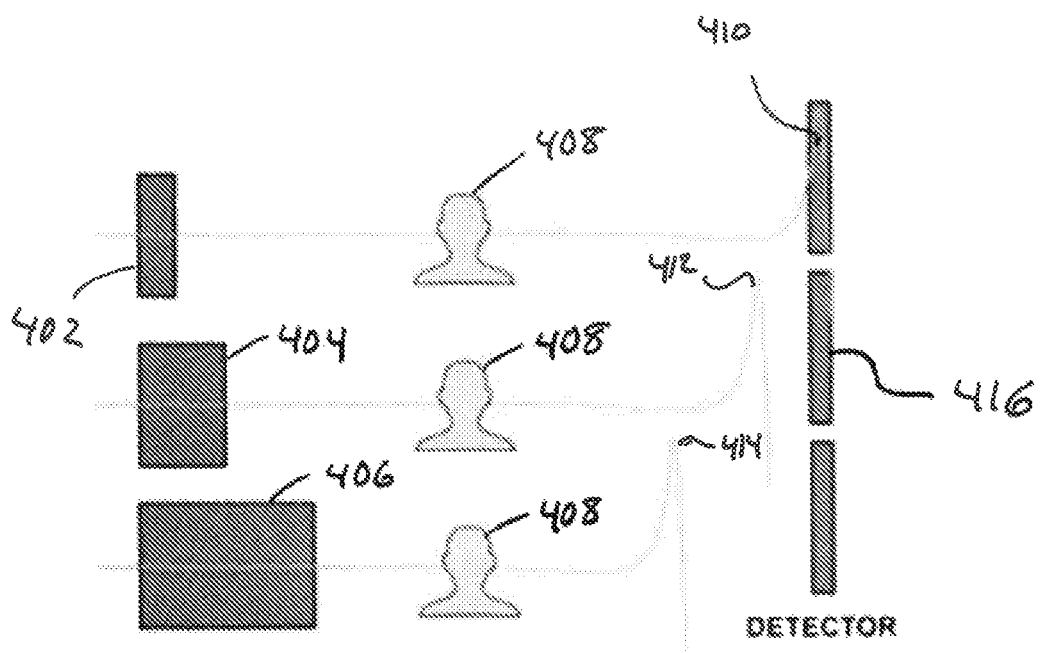
FIG. 4 is a block diagram illustration energy modulation of a proton beam.

FIG. 4 is a diagram that illustrates the effect of modulators having different WET values. In this example, modulator 402 may have the smallest WET value, modulator 404 may have an intermediate WET value, and modulator 406 may have the largest WET value of the three modulators shown. As a result, protons that pass through modulator 402 may exit modulator 402 with a higher energy level than protons that pass through modulator 404 because modulator 404 will dissipate more energy from the protons than modulator 402. Similarly, protons that pass through modulator 404 may exit modulator 404 with a higher energy level than protons that pass through modulator 406. Because the protons have different levels, their respective Bragg peaks will occur at different locations. The proton that passes through modulator 402 has the highest energy level, thus its Bragg peak 410 occurs at a location further than Bragg peak 412 and 414. The proton that passes through modulator 404 has an intermediate energy level, thus its Bragg peak 412 occurs at a location between Bragg peaks 410 and 414. And the proton that passes through modulator 406 has the lowest energy, thus its Bragg peak 414 occurs before Bragg peaks 410 and 412.

The variation in proton energy levels and the resulting difference in Bragg peak location can be detected by detector 416 to produce an image of patient 408.

One reason to modulate the proton beam is so that the proton beam imaging system can create a dosage rate function on the proton detector 416 for each pixel of the created image. The dosage rate function is the curve representing the dose measured by the detector pixels vs time. It is created by modulating the incident proton beam energy. The dose measured on the detector is maximum when the Bragg peak lands on the detector 410 and is produced by the modulator having a WET 402. As the modulator varies in WET 404 & 406 vs time, the dose on the detector varies in time.

The material and tissue of patient 408 that the proton beam passes through may have different water equivalent path lengths (WEPL). For example, bone may have a different WEPL than organ tissue, which may have a different WEPL than muscle tissue, etc. These different tissues may dissipate different amounts of energy from the proton beam, which may result in different dosage rate functions at the pixels receiving protons passing through that portion of the patient. These dosage rate functions at each pixel may be compared to calibration data consisting of dosage rate functions for known WET values. Thus, to create an accurate image, it is desirable to use this comparison to calculate the WEPL (water equivalent path length) from each pixel and reconstruct an overall image based on WEPL vs x and y. This WEPL image may result in a more accurate calculation of the relative stopping power (RSP) of the proton beam for treatment than current conversion from computed tomography (CT) images.

Figure 5:
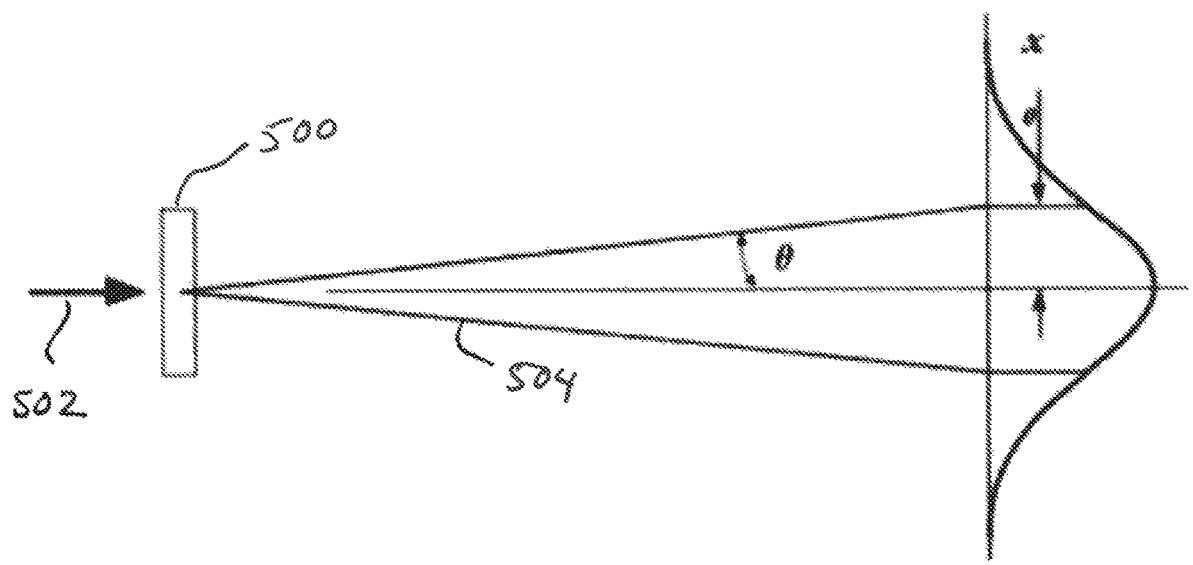
FIG. 5 is a diagram illustrating scattering of a proton beam.

FIG. 5 is a diagram of proton beam scattering by a modulator 500. Along with energy dissipation described above, a proton beam may scatter, i.e. spread out, as it passes through material such as modulator 500. Beam 502 may be a columnar beam when it enters modulator 500. However, proton beam 504 exiting modulator 500 may be scattered by an angle θ. This may cause a lateral spread x.

Figure 6:
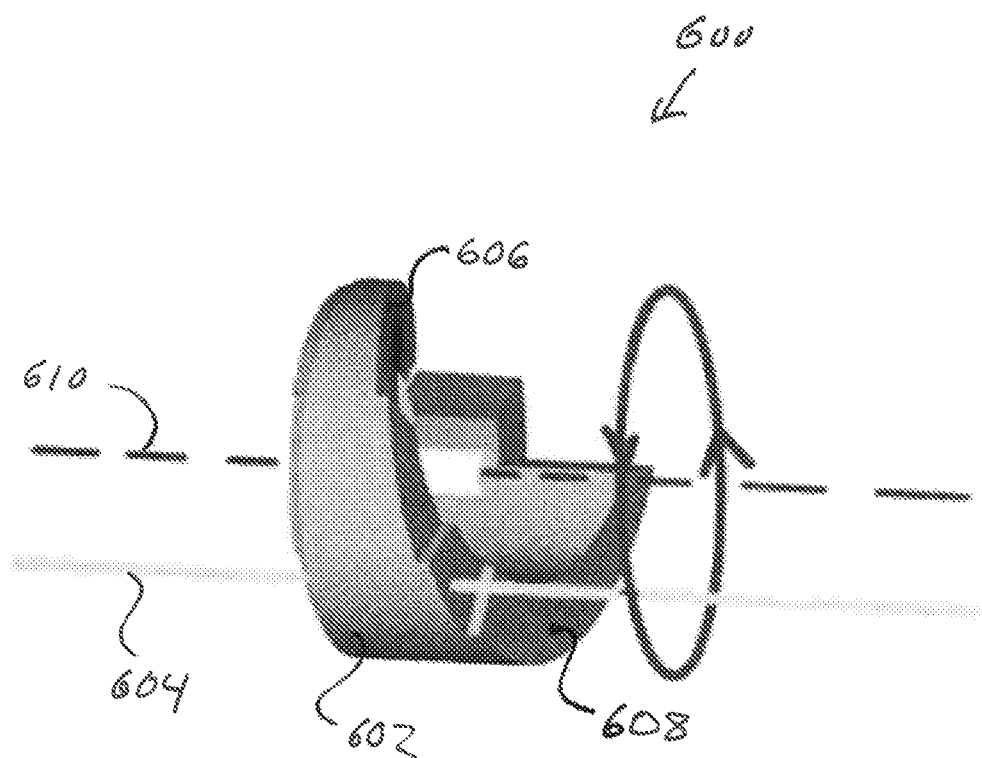
FIG. 6 is an isometric view of a proton beam modulator.

Referring to FIG. 6, a proton beam modulator 600 of the prior art includes a cylindrical body 602 through which proton beam 604 passes. Body 602 has a thickness that varies around the body's circumference. For example, body 602 is thicker at point 608 than it is at point 606. If beam 604 passes through body 602 at point 608, body 602 will dissipate more energy from beam 604 than if beam 604 passed through body 602 at point 606. The scattering effect at points 606 and 608 may also be different.

Proton beam modulator 600 may rotate about an axis 610, which may be parallel to and offset from proton beam 604. As modulator 600 rotates, proton beam 604 will pass through portions of body 602 with varying thickness. Thus, as modulator 600 rotates, the energy of beam 604 will vary.

Figure 7:
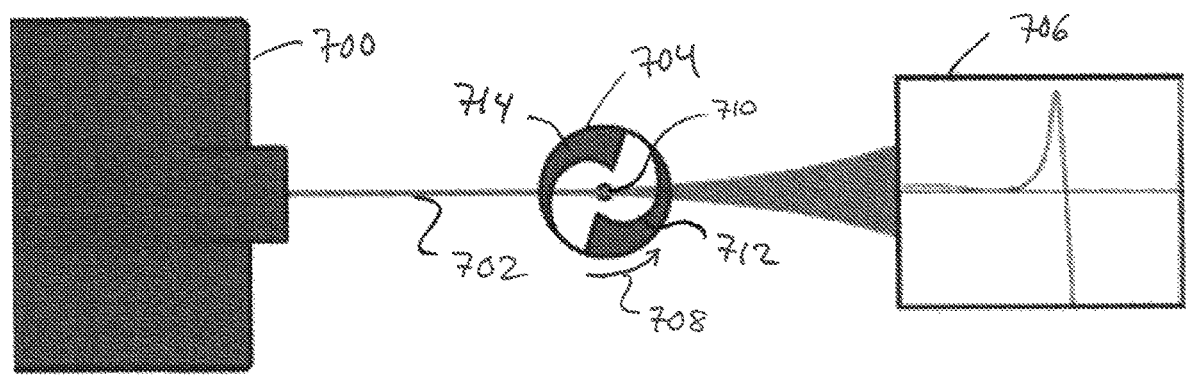
FIG. 7 is a block diagram of a proton beam imaging system including a proton beam modulator.

FIG. 7 is a block diagram of another embodiment of a proton beam imaging system. A proton beam generator 700 produces proton beam 702, which passes through modulator 704, through a target (not shown), and is detected by proton detector 706.

Proton beam modulator 704 may be a cylindrical modulator that rotates while beam 702 passes through it. In embodiments, the axis of rotation of modulator 704 may be perpendicular to beam 702 (i.e. in a direction into or out of the page) so that modulator 704 rotates in the direction of arrow 708. Also, modulator 704 may be positioned so that beam 702 passes through the center of rotation 710.

Proton beam modulator 704 may include two material sections 712 and 714 positioned so that beam 702 passes through section 712 and 714 as it passes through modulator 704. Material sections 712 and 714 may have variable thicknesses so that, as modulator 704 rotates, the thickness of the material that beam 702 passes through varies. As a result, as modulator 704 rotates, the thicker areas of material sections 712 and 714 will dissipate more energy from the proton beam and perform more scattering of the proton beam, so the energy level and scattering of beam 702 exiting the modulator will vary.

Figure 8:
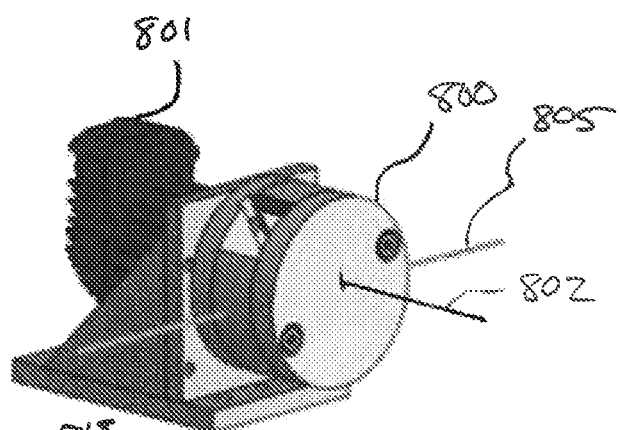
FIG. 8 is an isometric view of a proton beam modulator coupled to a drive system.
Figure 8A:
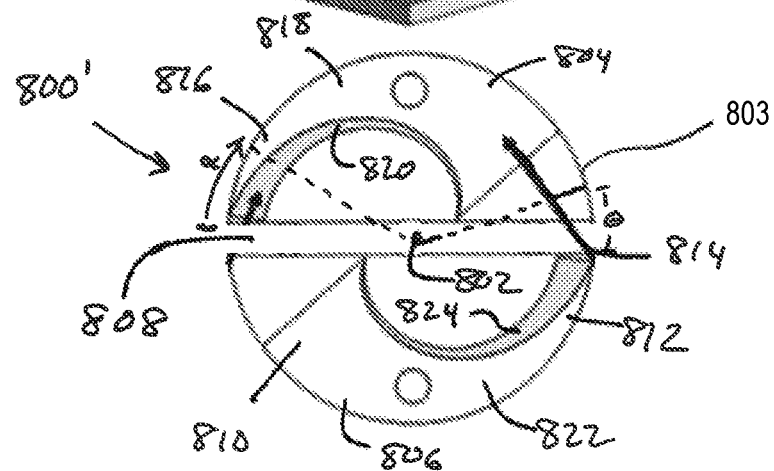
FIG. 8A is a side view of a proton beam modulator which may be the same as or similar to the proton beam modulator of FIG. 8.

Referring to FIGS. 8 and 8A, a modulator assembly 800 is mounted, or otherwise coupled or secured to, a drive system 801. In this illustrative embodiment, modulator assembly 800 is provided having a wheel-shape. Other shapes may, of course be used including but not limited to any regular or irregular geometric shape. Drive system 801 is capable of controlling the "spin" (i.e. the rate at which a modulator rotates around an axis of rotation) of at least a modulator 803 within modulator assembly 800. Specifically, modulator 801 is coupled to a shaft (e.g. a motor shaft) or other mechanical structure (not visible in FIG. 8) and drive system 801 turns the modulator 801 at a controllable and accurate rate of speed. In embodiments, drive system 801 is provided as a motor and modulator 801 is coupled to a motor shaft (not visible in FIG. 8).

As shown, modulator assembly 800 is disposed relative to a proton beam generator such that an axis of rotation 802 of modulator assembly 800 is perpendicular to an axis 805 along which a proton beam is aligned. During operation, motor 801 may rotate at least modulator 803. As a proton beam 805 passes through modulator assembly 800 (and in particular through modulators portions 804, 806), wedge-shaped modulators 804, 806 (FIG. 8A) intercept a proton beam 805. The configuration of the wedge-shaped modulators 804, 806 cause the energy level of proton beam 805 to vary after passing therethrough. Thus, the energy level of proton beam 805 may be varied during, for example, an imaging operation. The beam with varying energy levels may pass through a target (not shown in FIG. 8) and be detected by a proton beam detector (also not shown in FIG. 8). The detector may produce a signal representing the detected protons, which can be used by a processor to form an image of the target.

In embodiments, drive system 801 may be provided as a servo motor, or any other type of motor capable of precisely controlling the angular position and speed of rotation of the modulator within modulator assembly 800. It should, of course, be appreciated that any type of motor capable of rotating the modulator may, of course, also be used.

In one illustrative embodiment, drive system 801 may rotate modulator 800 at about 15 to about 20 rpms (i.e. one rotation every three to four seconds) or faster. In other embodiments, drive system 801 may rotate modulator 800 at about 180 rpm (i.e. a period of about 300 ms) or faster. This allows the modulator to sweep the energy level from the highest to the lowest energy level (or vice versa) in the time that it takes a person to take a breath. This may be beneficial if, for example, the proton beam imaging system is collecting an image of a patient's lung or other movable body area. If the full sweep of modulation occurs within a few seconds, or within a few hundred milliseconds, the imaging system may be able to capture an image before much body movement has occurred.

Referring now to FIG. 8A modulator 803 includes a plurality of material sections (with two wedge-shaped material sections 804 and 806 shown in the illustrative embodiment of FIG. 8A) positioned about axis of rotation 802. In embodiments, material sections may be placed symmetrically about axis of rotation 802 so that modulator 803 is balanced during rotation, which may help reduce rotational vibration. As beam 805 passes through material sections (e.g. material sections 804 and 806 in the illustrative embodiment of FIG. 8A), the material sections may modulate and scatter beam 805 as described above.

The material sections may be provided having a shape such that when they are appropriately positioned, a straight, open channel 808 exists through modulator 803. When modulator 803 is rotated so that channel 808 is parallel to beam 805, beam 805 may pass through channel 808 without passing through the material sections. In other words, when channel 808 is parallel to beam 805, beam 805 may pass through modulator 803 without being modulated. This may be useful if it is desired to use the same proton beam for imaging and radiation delivery. For example, modulator 803 can modulate the beam as it passes through material sections 804 and 806 for imaging. Then, for radiation dosage delivery, modulator 800 may rotate to a position that allows beam 805 to pass through channel 808 without being modulated. In this position, the unmodulated proton beam 805 may be used to deliver doses of radiation that are higher in energy than the modulated beam to target tissue.

In some applications, lower proton beam energies are used for treatment than for imaging. For example, a beam with lower energy may deliver its Bragg peak (and its resulting energy) within the patient at the site of treatment, rather than passing through the patient to be detected by the proton detector. If a lower proton beam is needed for treatment, it may seem counterintuitive to use open channel 808 during treatment because open channel 808 does not dissipate energy from beam 805. However, in embodiments, the proton beam treatment system may include another modulator specifically for modulating beam 805 during treatment. In these systems, the open channel 808 of modulator 800 may be used during treatment so that a separate treatment modular can be used to control the energy of beam 805 to deliver the proton beam's radiation to the treatment site within the patient.

In embodiments, material sections 804 and 806 may each have a curved wedge shape. The wedge shape may provide each material section with a thickness that varies along the length (e.g. along the shape) of each wedge. For example, material section 806 may have a thick end 810 and a thin end 812. Likewise, material section 804 may have a thick end 814 and a thin end 816. The thicker areas may provide more energy dissipation than the thin ends. Thus, a proton passing through thick portion 810 and thick portion 814 may exit modulator 803 with a lower energy level than a proton passing through thin portions 812 and 816. As modulator 803 spins, the thickness of the material through which proton beam 805 varies, and thus the energy level of proton beam 805 exiting modulator 800 will vary.

Material section 804 may comprise a first material 818 and a second material 820 coupled together to form the shape of material section 804. Similarly, material section 806 may comprise a first material 822 and a second material 824 coupled together to form the shape of material section 806. In embodiments, material 818 and material 822 may be the same material. Likewise, material 820 and material 824 may be the same material. In other embodiments, the materials may vary.

Materials 818 and 820 of material section 804 may be chosen so that, as modulator 803 rotates, modulator 803 will vary the energy level of proton beam 805 across a desired energy range and also maintain a relatively constant scattering angle of proton beam 805. For example, as proton beam 805 passes through thick portion 814 it will exit modulator 803 with less energy than when it passes through thin portion 816. However, the scattering of proton beam 805 will remain relatively constant whether it passes through thick portion 814 or thin portion 816. This effect can be achieved by the type of material and relative thicknesses chosen for material sections 818 and 820 (and material sections 822 and 824).

Different materials have different WET characteristics, as shown in table 1.

TABLE 1

| Material | Thickness (cm) | WET (cm) |
| --- | --- | --- |
| Lead | 4.5 | 25 |
| Aluminum | 11.9 | 25 |
| Human Tissue (lung) | 85.4 | 25 |
| Water | 25 | 25 |
| Titanium | 7 | 25 |
| Stainless-steel | 4.6 | 25 |

Table 1 shows the relative thickness of a material needed to achieve a WET characteristic of 25 cm. For example, lead having a thickness of about 4.5 cm will deplete the energy of a proton beam passing through it to the same degree as a tank of water with a thickness of 25 cm. Stainless-steel having a thickness of about 4.6 cm will deplete the energy of a proton beam passing through it to the same degree as a tank of water with a thickness of 25 cm.

Different materials may also have different scattering effects on proton beam 805. For example, a quantity of lead with a particular thickness may scatter beam 805 to a greater degree than a quantity of stainless-steel with the same thickness.

In embodiments, material 818 may be stainless-steel and material 820 may be lead. Similarly, material 822 may be stainless-steel and material 824 may be lead. Because lead and stainless-steel have similar WET values, it may be convenient to use them together in modulator 800 to perform modulation. However, any material may be used to perform the modulation so long as the material thickness is chosen to achieve the desired energy dissipation.

As shown in FIG. 8, the overall thickness of material section 804 (which comprises material 818 and material 820) tapers from relatively thick to relatively thin as angle θ increases. Similarly, the thickness of material 818 tapers from relatively thick to relatively thin as angle θ increases. Also, having an opposite taper, the thickness of material 820 tapers from thin to thick as angle θ increases.

If material section 804 consisted of a single type of material with varying thickness, then the energy level and the scattering effect of beam 805 may both vary as beam 805 traverses the single material. However, to achieve an accurate image from a proton beam imaging system, it may be desirable to vary the energy level of beam 805 while maintaining a relatively constant scattering of beam 805. Providing two materials having different scattering effects may allow modulator 800 to achieve this goal.

As noted above, lead and stainless-steel have similar WET characteristics for dissipating energy from proton beam 805. In contrast, lead and stainless-steel may have different scattering effects on beam 805. Lead, for example, may provide more scattering than stainless-steel for a given thickness of material. As such, material section 804 may comprise both lead and stainless-steel sections. For example, as beam 805 passes through thick portion 814, stainless-steel section 818 may provide a relatively large amount of energy dissipation and scattering. As beam 805 passes through thin portion 816, stainless-steel section 818 may provide a relatively small amount of energy dissipation and scattering. Lead section 820, which may provide more scattering per cm of thickness than stainless-steel, may be relatively thicker at end 816 to compensate for the lack of scattering at end 816. Thus, the combination of materials may provide reduced energy dissipation and relatively constant scattering as angle θ increases.

As noted above, beam 805 may pass through both material sections 804 and 806. Thus, beam 805 may pass through stainless-steel section 818, lead section 820, lead section 824, and stainless-steel section 822 as it passes through modulator 800. The effects of these sections on beam 805 may be additive. For example, if at a given point where beam 805 is passing through the modulator, the thickness of stainless-steel section 818 is 1 cm and the thickness of stainless-steel section 822 is 1 cm, the energy dissipation and scattering effect provided by these two sections may be the same or similar to a single stainless-steel section with 2 cm thickness. The same additive characteristic may be true for lead sections 820 and 824. Thus, the sum of the thicknesses of material sections 818, 820, 822, and 824 may be chosen so that the sections, in combination, provide the desired modulation and scattering effects.

Although modulator 800 is shown with stainless-steel sections positioned along the outside circumference and lead sections positioned closer to axis of rotation 802, any placement of the materials may be used to achieve the desired dissipation and scattering effects. For example, the lead sections could be placed along the outside circumference and the stainless-steel sections could be placed closer to axis of rotation 802. Also, although the stainless-steel and lead sections are shown in direct contact with one another, in other embodiments there may be an air gap between the lead and stainless-steel sections. Additionally, although stainless-steel and lead are used as example materials, other materials may also be used to achieve the desired dissipation and scattering effects. In each of these alternate embodiments, the thickness of each material section may be altered and/or chosen so that the desired dissipation and scattering effects are achieved.

In embodiments, material sections 804 and 806 need not be wedge-shaped. Other shapes (such as a sine wave shape, a triangle shape, etc.) may provide other modulation profiles if desired. In other embodiments, the thickness of material sections 804 and 806 is shown in the thickness profile of FIG. 10, which will be discussed below.

Figure 9:
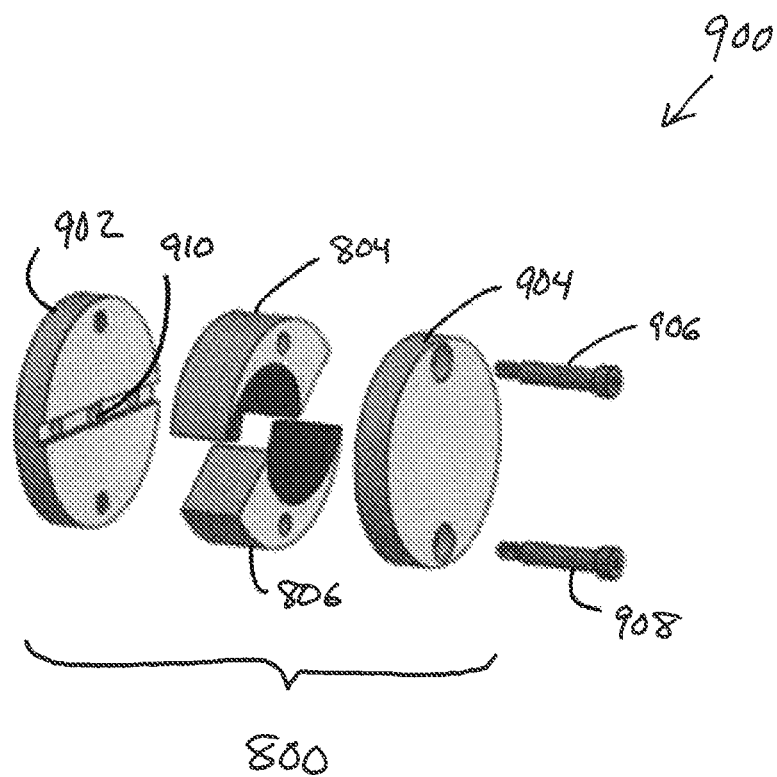
FIG. 9 is an isometric, exploded view of a proton beam modulator assembly.

FIG. 9 is an exploded isometric view of a portion 900 of a modulator assembly 800 (FIG. 8). In an embodiment, modulator assembly 800 (FIG. 8) comprises an inner plate 902 (here shown as a wheel-shaped inner plate 902) and an opposite, outer plate 904 (here shown as a wheel-shaped outer plate 904). Wedge-shaped material sections 804 and 806 (which together form modulator 803) are secured between plates 902 and 904. It should be appreciated that inner and outer plates may be provided having any shape suitable to secure the modulator 803.

In embodiments, wedge-shaped material sections 804 and 806 may be secured between plates 902 and 904 using any securing, mounting or fastening technique known to those of ordinary skill in the art. In the illustrative embodiment of FIG. 9, bolts 906 and 908 which pass through holes in plate 904 and material sections 804 and 806 are used. Bolts 906 and 908 may engage threaded holes in plate 902 and may be tightened to secure plates 902 and 904 and material sections 804 and 806 in desired positions. In embodiments, modulator 800 includes additional bolts or pins through material sections 804 and 806 so they do not pivot out of place. Bolts 906 and 908 may be made from the same type of stainless-steel as material sections 818 and 822 so that they do not create inconsistencies in beam dissipation when beam 805 passes through bolts 906 and 908.

Plate 902 may also include a hole 910 at the axis of rotation that can be used to mount modulator 800 on a motor spindle or shaft. A modular design such as the one shown in exploded view 900 may allow a user to easily swap components. For example, material sections 804 and 806 may be swapped for sections having other types of materials and shapes. Also, modulator assembly 800 (or just a modulator portion of a modulator assembly such as assembly 800) may be de-coupled or otherwise removed from motor 801 and replaced with another modulator and/or modulator assembly which provides a different modulation profile if needed for a particular application.

Figure 10:
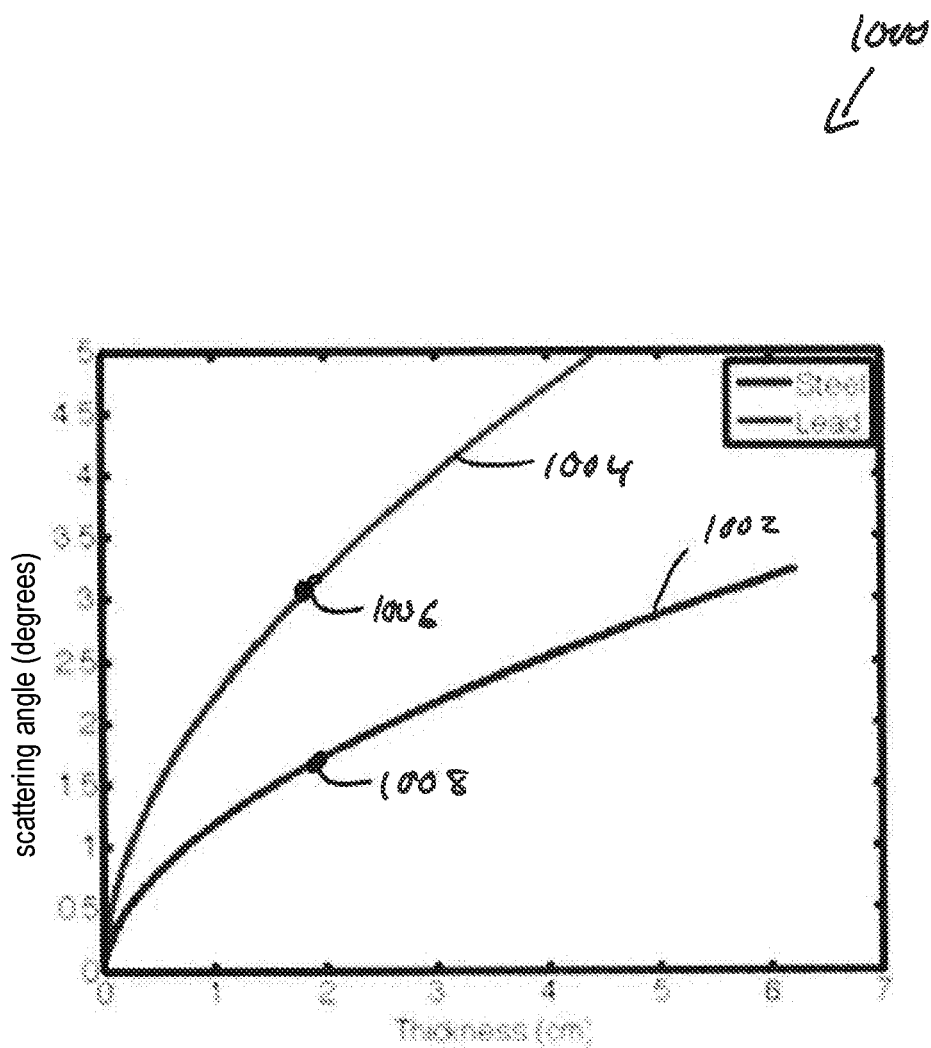
FIG. 10 is a graph of proton beam scattering versus material thickness.

FIG. 10 is a graph 1000 of material thickness versus scattering angle. The horizontal axis represents material thickness in cm. The vertical axis represents proton beam scattering angle in degrees. Curve 1002 is a scattering profile for stainless-steel and curve 1004 is a scattering profile for lead. As shown (and as discussed above) lead provides more scattering at a given thickness than stainless-steel. For example, 2 cm of lead causes approximately 3 degrees of scattering while 2 cm of stainless-steel causes approximately 1.5 degrees of scattering (see points 1006 and 1008, respectively).

Figure 11:
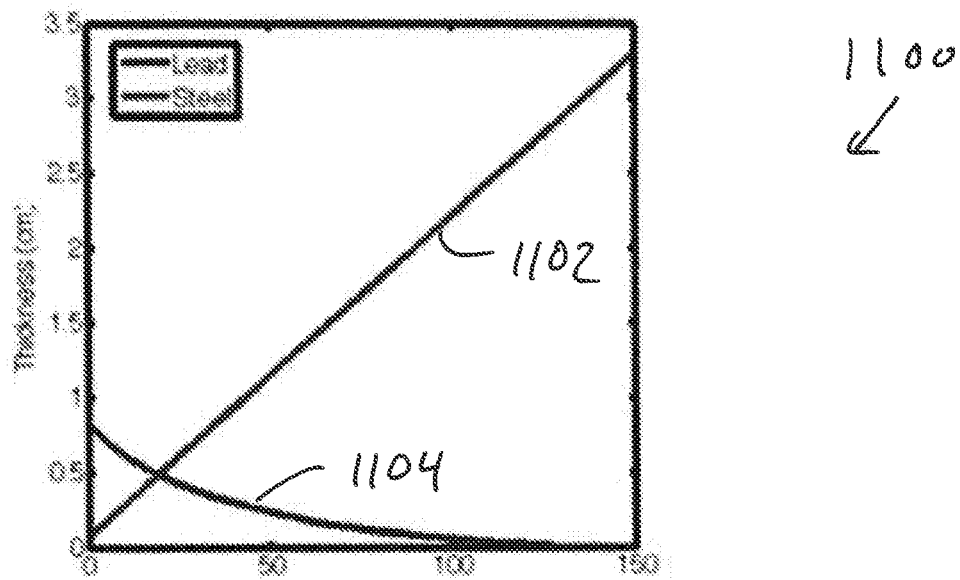
FIG. 11 is a graph of material thicknesses versus angular position of a proton beam modulator.

FIG. 11 is a graph 1100 that illustrates a thickness profile for material sections 818 and 820 (and/or material sections 822 and 824). (See FIG. 8). The horizontal axis represents the angle α and the vertical axis represents radial thickness in cm. Curve 1102 represents the thickness of stainless-steel section 818. As angle α increases from 0 to 150, the thickness of section 818 increases linearly from about 0 cm to about 3.2 cm. Curve 1104 represents the thickness of lead section 820. As angle α increases from 0 to 150, the thickness of section 818 decreases from about 0.7 cm to about 0 cm. In embodiments, curve 1104 may approximate an exponential decay. FIG. 11 illustrates thicknesses for one embodiment of modulator 800. Other thicknesses and shapes may also be used.

Figure 12:
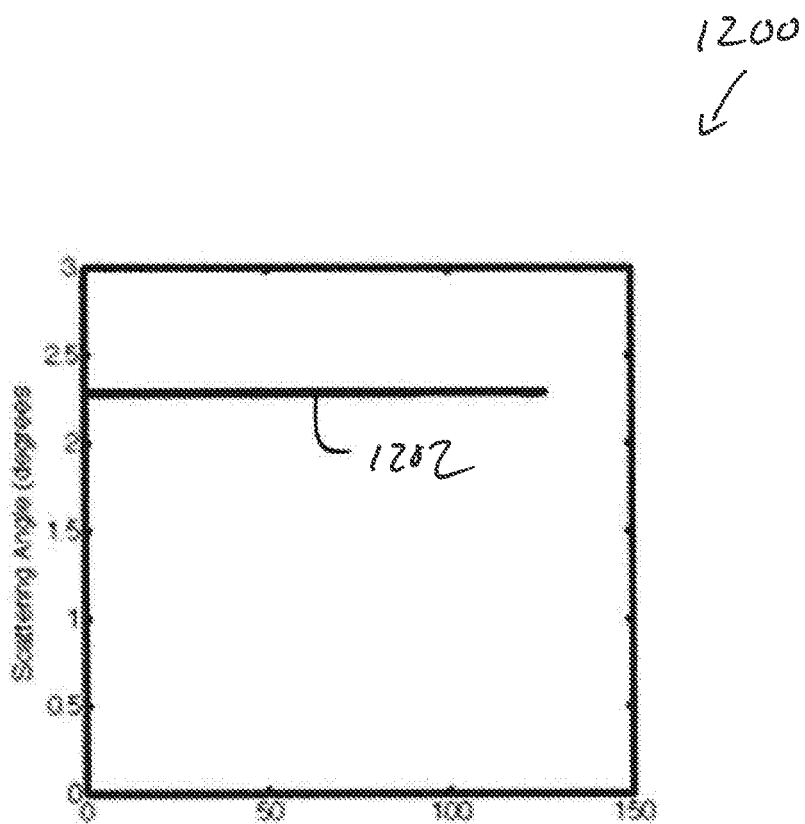
FIG. 12 is a graph of proton beam scattering versus angular position of a proton beam modulator.

FIG. 12 is a graph 1200 that illustrates a scattering effect (curve 1202) for a modulator (e.g. modulator 800) with the material thickness profile shown in graph 1100. The horizontal axis represents the angle α and the vertical axis represents scattering angle of a proton beam passing through modulator 800 at angle α. As angle α increases, the proton beam scattering angle stays relatively constant at about 2.3 degrees.

Figure 13:
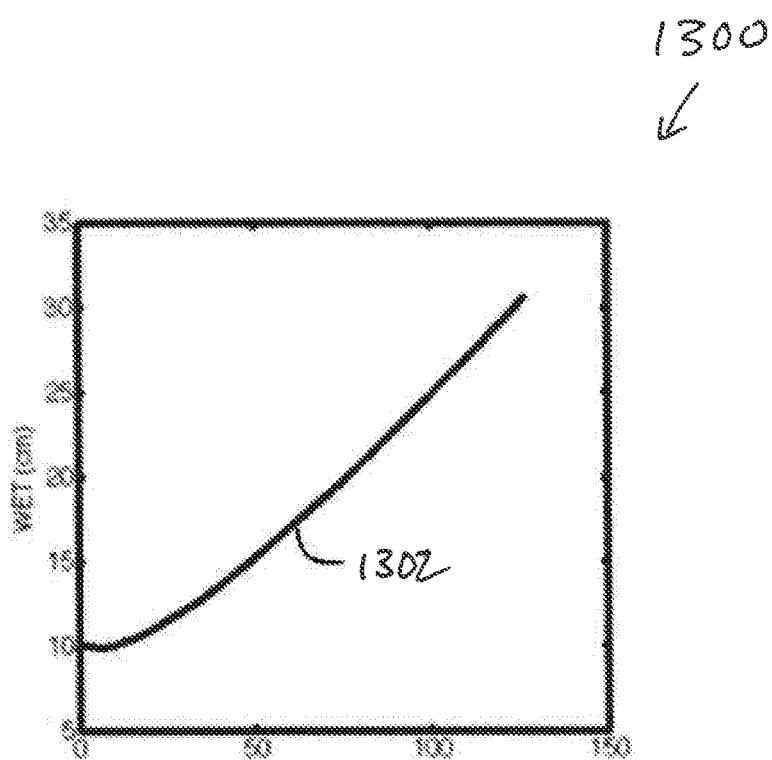
FIG. 13 is a graph of a WET characteristic versus angular position of a proton beam modulator.
Figure 14:
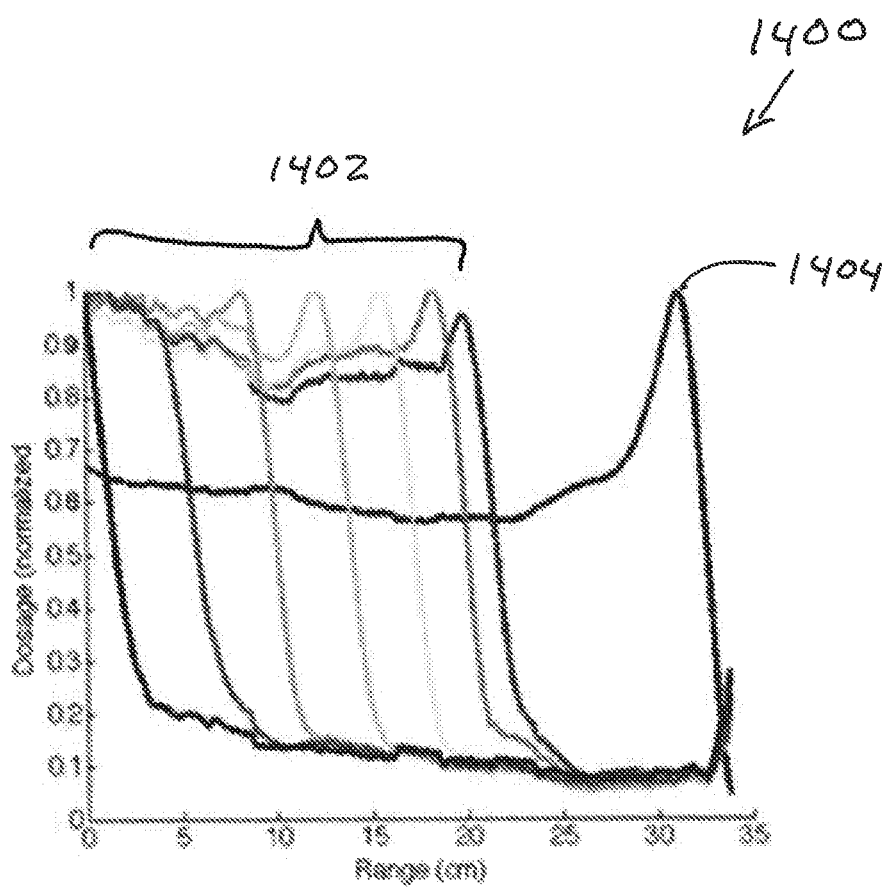
FIG. 14 is a graph of radiation delivery of a proton beam imaging system.

FIG. 13 is a graph 1300 that illustrates proton beam energy modulation for a modulator (e.g. modulator 800) with the material thickness profile shown in graph 1100. The horizontal axis represents the angle α and the vertical axis represents the WET characteristic of modulator 800 as seen by a proton beam entering modulator 800 at angle α. As angle α increases (i.e. as the thickness of the material through which the proton beam passes increases), the WET characteristic of modulator 800 increases approximately linearly from about 10 WET to about 30 WET. In other embodiments, the WET characteristic of modulator 800 may range from less than about 12 WET to more than about 32 WET FIG. 14 is a graph 1400 of measured test results that illustrate Bragg peaks of a proton beam passing through modulator 800 during operation. In this example, after exiting the modulator, the proton beam enters a tank of water (or, in this case, test equipment that simulates a tank of water). The horizontal axis represents the depth that the protons travel in the water tank. The vertical axis represents arbitrary units of energy released by the protons. As shown, as modulator 800 operates, Bragg peaks 1402 can be seen ranging between 0 cm and about 25 cm in the water tank. In other embodiments, Bragg peaks 1402 may range between about 12 cm WET to about 32 cm WET. Bragg peak 1404 corresponds to the unmodulated proton beam that passes through open channel 808 without passing through material section 804 or 806. (See FIG. 8). Thus, because they are unmodulated, the proton or protons that generate Bragg peak 1404 have a significantly higher energy level.

Having described various embodiments, which serve to illustrate various concepts, structures and techniques, which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims. All references cited in this document are incorporated here by reference in their entirety.

The invention claimed is:

1. A proton beam modulator comprising:
a first modulating portion comprising a first material portion and a second material portion, the first and second materials provided having characteristics such that in response to a proton beam incident thereon, at least portions of the proton beam pass therethrough; and
a second modulating portion comprising a third material portion and a fourth material portion provided having characteristics such that in response to the proton beam incident thereon, at least portions of the proton beam pass therethrough;
wherein the first and second modulating portions are symmetrically disposed about an axis of rotation of the proton beam modulator,
wherein the combination of the first, second, third, and fourth material portions modulate an energy level of the proton beam and a scattering of the proton beam, wherein the scattering remains substantially constant as the modulator rotates.

2. The proton beam modulator of claim 1 wherein the first modulating portion and the second modulating portion are positioned to create an open channel through the modulator so that, when the channel is parallel to the proton beam, the proton beam can pass through the open channel without passing through the first and second modulating portion.

3. The proton beam modulator of claim 1 wherein the first modulating portion has a wedge shape.

4. The proton beam modulator of claim 3 wherein the first material portion and the second material portion are arranged radially from the axis of rotation so that the second material portion is inside the first material portion.

5. The proton beam modulator of claim 3 wherein a thickness of the wedge shape decreases along an angular coordinate of the wedge shape.

6. The proton beam modulator of claim 5 wherein a thickness of the first material portion decreases along the angular coordinate of the wedge shape and a thickness of the second material portion increases along the angular coordinate of the wedge shape.

7. The proton beam modulator of claim 1 wherein the combination of the first, second, third, and fourth material portions modulate the energy level of the proton beam such that the energy level of the proton beam changes as the modulator rotates.

8. The proton beam modulator of claim 1 wherein the first and second modulating portions produce an energy modulation in the range of about 12 cm WET to about 32 cm WET.

9. The proton beam modulator of claim 1 wherein the first and third material portions comprise stainless-steel.

10. The proton beam modulator of claim 1 wherein the second and fourth material portions comprise lead.

11. The proton beam modulator of claim 1 wherein:
the first and third material portions comprise a first type of material;
the second and fourth material portions comprise a second type of material; and
the second material portion is positioned between the first material portion and an axis of rotation of the proton beam modulator, and the fourth material portion is positioned between the third material portion and the axis of rotation of the proton beam modulator.

12. The proton beam modulator of claim 1 further comprising a rotating wheel whereupon the first and second modulating portions are positioned opposite each other.

13. The proton beam modulator of claim 12 wherein the rotating wheel is positioned so that the proton beam passes through a center of rotation of the rotating wheel.

14. The proton beam modulator of claim 12 wherein the rotating wheel is positioned so that an axis of rotation of the rotating wheel is perpendicular to the proton beam.

15. The proton beam modulator of claim 12 further comprising a circular plate positioned so that the first modulating portion and the second modulating portion are sandwiched between the rotating wheel and the circular plate.

16. The proton beam modulator of claim 15 wherein the first and second modulating portions are removable from the rotating wheel and the circular plate.

17. The proton beam modulator of claim 12 wherein the rotating wheel has a diameter of 10 cm or less.

18. A proton beam imaging system comprising:
a proton beam generator to generate a proton beam;
a proton beam modulator through which the proton beam passes positioned between the proton beam generator and an image target; and
a proton beam detector positioned to detect the proton beam exiting the image target;
wherein the proton beam modulator comprises:
- a rotating wheel having an axis of rotation positioned so that the proton beam passes through the axis of rotation and the axis of rotation is perpendicular to the proton beam;
- a first modulating portion comprising a first material portion and a second material portion through which a proton beam passes; and
- a second modulating portion comprising a third material portion and a fourth material portion through with the proton beam passes;
- wherein the first and second modulation portions are positioned opposite each other on the rotating wheel,
- wherein the first, second, third, and fourth material portions comprise a wedge shape having a varying thickness to modulate an energy level of the proton beam as the proton beam modulator rotates, wherein the proton beam is modulated to have a substantially constant degree of scattering as the proton beam modulator rotates.

19. The proton beam imaging system of claim 18 wherein the first and third material portions comprise stainless-steel, and the second and fourth material portions comprise lead.

20. The proton beam imaging system of claim 18 further comprising a gantry portion, wherein the proton beam modulator is situated within the gantry portion.

21. A proton beam modulator comprising:
a plurality of wedge-shaped modulating portions, each of the plurality of wedge-shaped modulating portions comprising a first material portion and a second material portion disposed on a surface of the wedge-shaped modulating portions such that in response to a proton beam incident thereon, at least portions of the proton beam are capable of passing therethrough and wherein the plurality of wedge-shaped modulating portions are disposed in spatial relation such that the plurality of wedge-shaped modulating portions define an axis of rotation positioned such that an axis along which a proton beam is aligned perpendicular to the axis of rotation defined by the plurality of wedge-shaped modulating portions,
wherein the first material portion and the second material portion are arranged radially from the axis of rotation so that the second material portion is inside the first material portion.

22. The proton beam modulator of claim 21 wherein the plurality of wedge-shaped modulating portions are provided as a pair of modulating portions positioned opposite each other to define an axis of rotation positioned such that an axis along which a proton beam is aligned is perpendicular to the axis of rotation defined by the pair of wedge-shaped modulating portions.

* * * * *